United States Patent [19]

Aki et al.

[11] Patent Number: 5,443,834
[45] Date of Patent: Aug. 22, 1995

[54] SOAP COMPOUNDED WITH VITAMIN $B_1$-CONTAINING GARLIC EXTRACT

[75] Inventors: Osami Aki, Kawanishi; Rikujiro Kashi, Kawaguchi; Kanji Nakatani, Tokyo; Atsunori Okada, Mitoyo, all of Japan

[73] Assignees: Fuji Sangyo Kaisha, Ltd., Kagawa; Takeda Chemical Industries, Ltd., Osaka, both of Japan

[21] Appl. No.: 164,824

[22] Filed: Dec. 9, 1993

Related U.S. Application Data

[63] Continuation of Ser. No. 847,308, Mar. 6, 1992, abandoned.

[30] Foreign Application Priority Data

Mar. 8, 1991 [JP]   Japan ................................ 3-043484

[51] Int. Cl.⁶ .............................................. A61K 7/48
[52] U.S. Cl. ................................... 424/401; 424/405; 424/409; 424/195.1; 424/526; 514/558
[58] Field of Search .................... 424/401, 405, 409; 514/858–865

[56] References Cited

U.S. PATENT DOCUMENTS 1,492,367  4/1924  Franck-Philipson ............... 424/405
5,006,337  4/1991  Motitschke et al. ............. 424/195.1

FOREIGN PATENT DOCUMENTS 3328810  2/1984  Germany ............................ 514/864

OTHER PUBLICATIONS

Hasegawa et al. in Skin Res 33(2) 1991 172–186 Abstract A Study of the Garlic Extract Vitamin B-1 Complex in The Treatment of Atopic Dermatitis.
Okada et al. in JP 62036153 17 Feb. 1987 Abstract Stable Vitamin $B_1$ Additive for fish feeds.
Okada Chem. Abstracts vol. 110:160249F p. 392, 1989 Bath Preparations Containing Allithiamine or Allithiamine-containing garlic extracts.
Kimura et al., Vitamins (Japan), 63(12) 621–625 (1989).

Primary Examiner—Thurman K. Page
Assistant Examiner—Neil Levy
Attorney, Agent, or Firm—Wenderoth, Lind & Ponack

[57] ABSTRACT

A composition of soap compounded with a garlic extract containing thiamine, a thiamine derivative having vitamin $B_1$ activity or a salt thereof is disclosed. The soap is effective for improving atopic dermatitis.

14 Claims, No Drawings

SOAP COMPOUNDED WITH VITAMIN $B_1$-CONTAINING GARLIC EXTRACT

This application is a continuation of now abandoned application, Ser. No. 07/847,308, filed Mar. 6, 1992.

FIELD OF THE INVENTION

The present invention relates to a composition comprising soap compounded with a vitamin $B_1$-containing garlic extract which is effective for improving atopic dermatitis.

BACKGROUND OF THE INVENTION

It has been known that a vitamin $B_1$-containing garlic extract is effective for improving atopic dermatitis, and bath salts formulated with a composition of a vitamin $B_1$-containing garlic extract as an effective component have been proposed (JP-A 63-307812) and marketed for assisting treatment of atopic dermatitis. Further, since bath salts compounded with a vitamin $B_1$-containing garlic extract have good humectant effect, they are also used for healthy persons. However, since bath salts are put into a bathtub, it is difficult to limit their use to a particular person. Then, their use is restricted depending upon individual difference in preference for odor of garlic. In addition, many people do not take a bath everyday, especially, in summer, although they take a shower, and the effect of such bath salts is not necessarily sufficient.

On the other hand, unlike bath salts, soap can be used individually and can be used when a person washes his face, etc. or takes a shower. Thus, soap can be readily used without taking a bath. However, no soap compounded with a vitamin $B_1$-containing garlic extract has been found heretofore in the prior art.

OBJECTS OF THE INVENTION

The main object of the present invention is to provide a composition comprising soap compounded with a vitamin $B_1$-containing garlic extract.

This object as well as other objects and advantages of the present invention will become apparent to those skilled in the art from the following description.

SUMMARY OF THE INVENTION

According to the present invention, there is provided a composition comprising soap compounded with a garlic extract containing thiamine, a thiamine derivative having vitamin $B_1$ activity or a salt thereof.

DETAILED DESCRIPTION OF THE INVENTION

The thiamine derivative having vitamin $B_1$ activity used in the present invention is a thiamine derivative which is readily absorbed in the intestinal tract, is readily delivered to the tissues, is long lasting and is readily converted to thiamine in the living body. Examples thereof are thiamine derivatives having a disulfide bond such as allithiamine, thiamine propyldisulfide, thiamine tetrahydrofurfuryl disulfide, octotiamine, thiamine disulfide, bisbentiamine, bisbutitiamine, bisibutiamine and thiamine monophosphate disulfide. Further examples of the thiamine derivative are thiamine pyrophosphate, benfotiamine, dicethiamine, cycotiamine and the like.

Examples of the salt of thiamine and its derivative include hydrochloric acid salt, nitric acid salt and the like.

The garlic extract to be used in the present invention containing thiamine, the derivative thereof having vitamin $B_1$ activity or the salt thereof (sometimes hereinafter referred to as merely "thiamine and the like") is readily prepared by mixing the thiamine and the like with a garlic extract.

For example, allithiamine can be formed by mixing vitamin $B_1$ with a garlic extract under appropriate conditions such as those disclosed in the above JP-A 63-307812 and, therefore, allithiamine-containing garlic extract can be obtained efficiently, for example, according to the following method:

First, garlic is ground and squeezed according to a conventional manner to obtain garlic juice. A vitamin $B_1$ salt (e.g., hydrochloric acid salt, nitric acid salt, etc.) is added to the garlic juice in an amount of 0.05 to 3.0% by weight, preferably, 0.5 to 2.0% by weight based on the raw garlic. The mixture is adjusted to pH 6.0 to 9.0, preferably, pH 7.0 to 8.5. Then, the mixture is warmed at a temperature of 50° to 70° C., preferably, 55° to 65° C. for 5 minutes to 4 hours, preferably, 30 minutes to 2 hours. Immediately after warming, the precipitate formed is removed by filtration or centrifugation to obtain almost odorless allithiamine-containing garlic extract.

When the amount of vitamin $B_1$ added, pH, temperature and time of warming are less than the above lower limit, respectively, the formation of allithiamine is insufficient. On the other hand, when they exceed the above upper limit, components of the garlic extract could be changed in quality. When the precipitate formed is removed by filtration or centrifugation, if necessary, a filter aid such as Celite, Pearlite or the like, as well as a protein coagulant such as calcium chloride, magnesium chloride or the like can be used. Further, proteins can also be precipitated by adjusting to pH 3 to 5.

The amount of the garlic extract containing thiamine or the like is not specifically limited. Normally, the desired effect can be obtained when the soap is compounded with the garlic extract in an amount of about 0.05 to 1.0% by weight based on the total weight of the soap.

The soap of the present invention can be in a conventional form such as solid soap, liquid soap, cream soap (mousse type soap) or the like. Other components to be compounded can be any one normally used in conventional soap as long as the effect of the garlic extract is not influenced. Examples thereof include fats and oils (e.g., beef tallow, mutton tallow, palm oil, olive oil, coconut oil, castor oil, palm kernel oil, etc.), glycerin, a coloring agent, perfume, titanium oxide, a metal blocking agent, an antioxidant, a pharmacologically active agent other than the garlic extract, and the like.

The soap of the present invention can be prepared according to a conventional manner. That is, firstly, neat soap is prepared according to a conventional method such as saponification of fats and oils, salting-out, neutralization of fatty acids, saponification of fatty acid esters and the like. Then, the garlic extract is added to the neat soap and the resulting mixture is kneaded manually or mechanically to obtain the soap of the present invention. In particular, neutralization of fatty acids is preferred.

The soap of the present invention can be used for the same purpose in the same manner as those of conventional soap. In particular, the soap of the present invention is useful for assisting treatment of atopic dermatitis.

As described above, according to the present invention, there is provided soap compounded with garlic extract containing thiamine or the like, that is, a novel form of an article compounded with vitamin $B_1$-containing garlic extract. Unlike conventional bath salts, the soap of the present invention makes the individual use of vitamin $B_1$-containing garlic extract possible. Further, according to the present invention, the garlic extract can be readily used in everyday life.

Furthermore, like bath salts containing a composition of vitamin $B_1$-containing garlic extract, the soap compounded with vitamin $B_1$-containing garlic extract is useful for assisting treatment of atopic dermatitis and has high utility.

The following Examples and Experiments further illustrate the present invention in detail but are not to be construed to limit the scope thereof. All the "percents" are by weight unless otherwise stated.

EXAMPLE 1

Preparation of allithiamine-containing garlic extract

Raw garlic (5 kg) was ground and squeezed to obtain garlic juice. Thiamine hydrochloride (50 g) was added to the juice. The mixture was adjusted to pH 8 and warmed at 60° C. for 1 hour. Then, the mixture was centrifuged and the supernatant obtained was concentrated to dryness to obtain a powder extract (1 Kg).

Preparation of soap

Beef tallow and coconut oil (8:2) were used as raw fats and oils to prepare neat soap according to conventional neutralization of fatty acids. Tetrasodium edetate tetrahydrate (0.05%) and glycerin (1%) were added to the neat soap. The mixture was mixed and dried to obtain a soap base containing water in an amount of about 14%. The above powder extract (300 g), titanium oxide (300 g) and perfume (300 g) were added. The resulting mixture was mixed, kneaded and extruded into a stick material by using an extruder. The stick material was pressed and molded to obtain 700 cakes of the desired soap (100 g) compounded with the garlic extract.

EXAMPLE 2

According to the same manner as that described in Example 1, soap compounded with the garlic extract was prepared except that titanium oxide was not used.

EXAMPLE 3

Preparation of garlic extract

Vitamin $B_1$ hydrochloride (3.4 kg) was dissolved in water (20 liters). The pH of this solution was adjusted to about 8 with $NaHCO_3$ and stirred at room temperature. A solution of an alkyl bunte salt, i.e., propyl bunte salt ($CH_3CH_2CH_2SSO_3Na$) (1.8 kg) in water was added thereto. The resulting mixture was stirred for 30 minutes. The mixture was added to a garlic juice obtained by grinding raw garlic (120 kg) and squeezing the ground garlic. The resulting mixture was stirred and filtered. The filtrate was concentrated and dried to obtain a powder garlic extract (about 25 kg) containing thiamine propyldisulfide.

Preparation of soap

According to the same manner as that described in Example 1, soap compounded with a garlic extract containing the thiamine derivative having vitamin $B_1$ activity was prepared except that the above powder garlic extract containing thiamine propyldisulfide was used instead of allithiamine-containing garlic extract.

Experiment 1

Effect of the soap compounded with the garlic extract on improvement of atopic dermatitis was evaluated as follows by using the soap obtained in Example 1.

Subjects:

Subjects were 83 outpatients with atopic dermatitis (16 patients: 0 to 3 years old, 16 patients: 4 to 11 years old, 51 patients: 11 years old or older, their conditions were well recognized) at the Department of Dermatology at Osaka Medical College, Japan.

Method:

The patients used the soap compounded with the garlic extract of Example 1 instead of soap that they had been using. The soap was used when they took a bath daily for more than 2 weeks.

Combination of drugs:

The same drug was used as that which was used prior to using the soap of Example 1. Change of the drug was prohibited regardless of whether the symptoms of the subject became worse or better.

Evaluation of effect:

Overall evaluation of the soap's effect was carried out from three points of view, i.e., feeling during use of the soap, subjective degree of improvement and objective degree of improvement by rating each factor according to four criteria, i.e., markedly effective, moderately effective, slightly effective and ineffective. The evaluation was carried out by dividing the subjects into 3 groups, i.e., patients of 0 to 3 years old, patients of 4 to 10 years old and patients of 11 years old or older.

The results are shown in Table 1. The number in Table 1 is the total number of patients corresponding to the particular rating.

TABLE 1

| Atopy | Markedly effective | Moderately effective | Slightly effective | Ineffective | Total |
|---|---|---|---|---|---|
| 0–3 years old | 2 | 9 | 5 | 0 | 16 |
| 4–10 years old | 1 | 7 | 8 | 0 | 16 |
| 11 years old or older | 4 | 19 | 23 | 5 | 51 |
| Total | 7 (8.4%) | 35 (42.2%) | 36 (43.4%) | 5 (6.0%) | 83 |

As is clear from Table 1, 68.6% (11/16) of the patients of 0 to 3 years old, 50.0% (8/16) of the patients of 4 to 10 years old and 45.1% (23/51) of the patients of 11 years older have evaluated as "effective" or better. When the patients who have evaluated as "slightly effective" are included, 100% (16/16) of the patients of 0 to 3 years old, 100% (16/16) of the patients of 4 to 10 years old and 90.2% (46/51) of the patients of 11 years old or older have been evaluated as effective. Thus, good assisting effect of treatment of atopic dermatitis is observed.

At present, no side effects such as dermatitis have been found to be caused by the soap compounded with the garlic extract.

Experiment 2

Subjects:

Subjects were 50 outpatients with atopic dermatitis at Seiwakai Kyoritsu Hospital in Tokushima prefecture, Japan.

Method:

The soap of Example 1 was used for a week every day instead of using bath salts containing a composition of a vitamin $B_1$-containing garlic extract. The internal medicine and topical preparations were used according to the same manner as that before the use of the soap.

Results:

Overall evaluation was carried out with respect to improvement of appearance of the skin, improvement of itching, improvement of degree of dryness and the like. As a result, 8 patients (16%) evaluated as "markedly effective", 16 patients (32%) evaluated as "effective", 15 patients (30%) evaluated as "slightly effective" and 11 patients (22%) evaluated as "unchanged". Thus, effectiveness was 78% inclusive of "slightly effective".

What is claimed is:

1. A composition consisting essentially of solid soap compounded with a garlic extract containing thiamine or a thiamine derivative or a salt thereof having vitamin B, activity by mixing neat soap which consists essentially of beef tallow and coconut oil in a ratio of 8:2, said garlic extract, perfume and glycerin and kneading the mixture, said garlic extract being compounded in an amount of 0.05 to 1.0% by weight based on the total weight of said solid soap, and said thiamine or thiamine derivative or salt thereof being compounded in an amount of 0.05 to 3.0% by weight based on the weight of raw garlic used for preparing said garlic extract.

2. The composition according to claim 1, wherein the thiamine derivative has a disulfide bond.

3. The composition according to claim 2, wherein the thiamine derivative is allithiamine.

4. The composition according to claim 2, wherein the thiamine derivative is thiamine propyldisulfide.

5. The composition according to claim 2, wherein the thiamine derivative is thiamine tetrahydrofurfuryl disulfide.

6. The composition according to claim 2, wherein the thiamine derivative is octotiamine.

7. The composition according to claim 2, wherein the thiamine derivative is bisbentiamine.

8. The composition according to claim 2, wherein the thiamine derivative is bisbutitiamine.

9. The composition according to claim 2, wherein the thiamine derivative is bisibutiamine.

10. The composition according to claim 2, wherein the thiamine derivative is thiamine monophosphate disulfide.

11. The composition according to claim 1, wherein the thiamine derivative is thiamine pyrophosphate.

12. The composition according to claim 1, wherein the thiamine derivative is benfotiamine.

13. The composition according to claim 1, wherein the thiamine derivative is dicethiamine.

14. The composition according to claim 1, wherein the thiamine derivative is cycotiamine.

* * * * *